United States Patent [19]

Masuzawa et al.

[11] Patent Number: 4,791,118
[45] Date of Patent: Dec. 13, 1988

[54] QUINOLONECARBOXYLIC ACID DERIVATIVES AND THEIR PREPARATION

[75] Inventors: Kuniyoshi Masuzawa, Koga; Seigo Suzue; Keiji Hirai, both of Kuki; Takayoshi Ishizaki, Washimiya, all of Japan

[73] Assignee: Kyorin Pharmaceutical Co., Ltd., Tokyo, Japan

[21] Appl. No.: 903,424

[22] Filed: Sep. 4, 1986

[30] Foreign Application Priority Data

Sep. 21, 1985 [JP] Japan .................. 60-209447

[51] Int. Cl.⁴ .................... C07D 401/04; A61K 31/47
[52] U.S. Cl. ...................................... 514/312; 546/156
[58] Field of Search .................. 514/312; 546/156; 544/363

[56] References Cited

U.S. PATENT DOCUMENTS 4,578,473  3/1986  Domagala et al. ............... 546/156
4,599,334  7/1986  Petersen et al. ............... 544/363
4,638,067  1/1987  Culbertson et al. ............. 546/156

FOREIGN PATENT DOCUMENTS 0106489  4/1984  European Pat. Off. .
0153163  8/1985  European Pat. Off. .

OTHER PUBLICATIONS

Domagala, II et al., *J. Med. Chem.* 29 (4), pp. 448–453 (Apr. 1986).

*Primary Examiner*—Donald G. Daus
*Assistant Examiner*—E. Bernhardt
*Attorney, Agent, or Firm*—Oblon, Fisher, Spivak, McClelland & Maier

[57] ABSTRACT

Quinolonecarboxylic acid derivatives of the following formula,

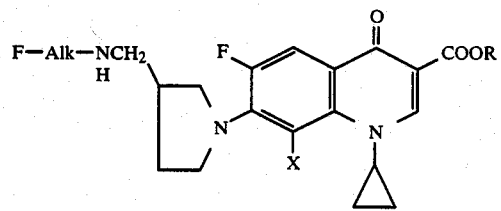

wherein R is hydrogen atom or lower alkyl group, Alk is lower alkylene group and X is hydrogen atom or halogen atom; the hydrates and pharmaceutically acceptable salts thereof are useful as antibacterial agent.

4 Claims, No Drawings

QUINOLONECARBOXYLIC ACID DERIVATIVES AND THEIR PREPARATION

DETAILED DESCRIPTION OF THE INVENTION

This invention is concerned with certain novel useful quinolonecarboxylic acid derivatives of the formula (I), with a process for their preparation and with compositions containing them.

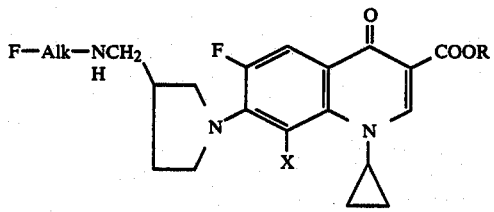

(I)

In the formula (I), R is hydrogen atom or lower alkyl group, Alk is lower alkylene group and X is hydrogen atom or halogen atom.

The term "lower alkyl group", as used herein, means alkyl radicals having from one to five carbon atoms such as methyl, ethyl, isopropyl and t-butyl group.

The term "lower alkylene group", as used herein, means alkylene radicals having from one to five carbon atoms, of which can be substituted by above mentioned lower alkyl group, as illustrated by ethylene, propylene, 2-methylpropylene and pentamethylene.

The term "halogen atom", as used herein, means fluorine, chlorine, bromine and iodine, especially fluorine and chlorine.

Since nalidixic acid which has been employed for treatment of urinary tract infections by gram-negative bacteria, was introduced in 1963, intensive work has been carried out on the further development of quinolonecarboxylic acid analogue.

Thus, recently a remarkable antibacterial activity against not only gram-negative bacteria but also gram-positive bacteria occurs for some compounds (e.g. norfloxacin). However their activity against gram-positive bacteria is fairly less than that against gram-negative bacteria.

Just recently, the drugs which have relatively strong activity against gram-positive bacteria (e.g. CI-934) have been developed, but shown to possess weaker activity against gram-negative bacteria than that of the prior compounds (e.g. norfloxacin, ciprofloxacin).

As a result of the investigation, the present inventors have now unexpectedly found that new derivatives of quinolonecarboxylic acid represented by the formula (I) have excitingly potential activity against gram-negative bacteria in comparison with that of any prior analogue and therefore are superior to commercial preparation and investigational drugs in the in vitro and in vivo antibacterial activity against gram-negative and gram-positive bacteria.

Furthermore, the compounds of this invention possess excellent antibacterial activity not only against aerobic bacteria but also against anaerobic bacteria and mycoplasmas.

The present compounds are well absorbed and distributed into the tissue when administered orally in animals.

The present compounds, therefore, are active at low doses against both gram-positive and gram-negative bacteria and thus constitute valuable agents for the treatment of infectious human, animal or plant diseases.

In following, explanation is made about the preparation process for the compound of the invention.

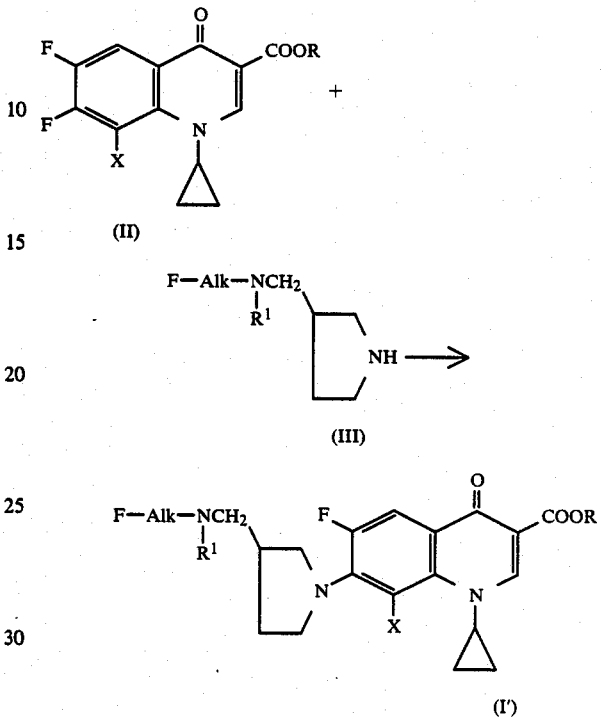

wherein $R^1$ is hydrogen atom or protective group, Alk, R and X have the above-stated meanings.

Namely, by allowing compounds represented by the formula (II) to react with amines presented by the formula (III), compounds represented by the formula (I') is synthesized. However, in the case of compounds wherein $R^1$ is protective group in the formula (III), e.g., $R^1$ is alkoxycarbonyl group, for example, methoxy, ethoxy, t-butoxy-, benzyloxycarbonyl group and the acyl group, e.g., formyl, acetyl, propionyl, benzoyl group and the like, the protective group is removed from the reactant represented by the formula (I') according to the usual method to give the compounds of this invention, wherein $R^1$ is hydrogen atom. The reaction of compounds represented by the formula (II) with amines represented by the formula (III) preferably is carried out by heating the mixture in a solvent such as water, alcohols, acetonitrile, dimethylformamide (DMF), dimethyl sulfoxide (DMSO), hexamethylphosphoric triamide, pyridine, picoline and the like or in the absence of the solvent. The reaction temperature is selected appropriately in a range of room temperature to 200° C., preferably room temperature to 160° C. In more details, it is preferable to allow compounds represented by the formula (II) to react with 1 to 5 times mole of compounds represented by the formula (III) for 1 to several hours at room temperature to 160° C. in 2 to 10 times volume of aforementioned solvents. At this time, the use of deacidifying agents such as triethylamine, diazabicyclo bases and potassium carbonate is also desirable. Moreover, compounds (I') wherein R is a lower alkyl group can be hydrolyzed to give the carboxylic acids according to the usual method. Such hydrolysis can be carried out easily with alkalies such as potassium hydroxide or acids such as sulfuric acid at room temperature to boiling point of solvents in water, mixed liquor of water with alcohols, mixed liquor of water with acetic acid, and so on.

Furthermore, the compounds of the formula (I) can be converted, if desired, to the pharmaceutically acceptable ammonium salts or carboxylic acid metal salts by treatment with acid or alkali. The acid may be organic or inorganic acids such as, for example, hydrochloric acid, sulfuric acid, phosphoric acid, acetic acid, methanesulfonic acid, oxalic acid and lactic acid. The carboxylic acid metal salts may be, for example, sodium, potassium, magnesium, calcium, aluminum, cerium, chromium, cobalt, copper, iron, zinc, platinum and silver salts.

The compound of the formula (I), hydrates and salts thereof may be used as medicines in the conventional form of pharmaceutical preparations, which may be, for example, tablets, capsules, powder, ointments, suppositories, injections or eye drops, suitable for peroral, parenteral, enteral or local administration.

The following examples will further illustrate the invention without, however, limiting it thereto.

REFERENCE EXAMPLE 1

3-(2-fluoroethyl)aminomethylpyrrolidine

To a solution of 1-benzyl-3-aminomethylpyrrolidine (J. Org. Chem. 26 4955, 1961; 5.0 g) in pyridine (30 ml) was added p-toluenesulfonyl chloride (5.6 g) for 5 minutes, and stirred for 2 hours at room temperature. After the reaction mixture was allowed to stand overnight and concentrated. The residue contain pyridine was removed by azeotrope with water (20 ml). A solution of the resulting residue in dichloromethane (100 ml) was washed with aqueous solution of potassium carbonate (x 2) and water, dried over anhydrous sodium sulfate and concentrated. The residue was purified by silica gel chromatography eluting with methanol:acetonitrile:dichloromethane (0:1:3→0.5:1:3) to give 1-benzyl-3-(p-toluenesulfonyl)aminomethylpyrrolidine (5.31 g) as liquid.

To a suspension of sodium hydride (55%/oil; 0.72 g) in absolute DMF (15 ml) was added slowly a solution of this oil (5.20 g) in absolute DMF (15 ml). After stirring for 30 minutes at room temperature, to the reaction mixture was added dropwise 2-fluoroethylbromide (2.11 g) for 5 minutes. After stirring for 4 hours, added 2-fluoroethylbromide (1.30 g) and stirring for further 3 hours. After the reaction mixture was allowed to stand overnight, the mixture was poured into ice-water (50 ml), extracted with chloroform, washed with water, dried over anhydrous sodium sulfate and concentrated to give 1-benzyl-3-[N-(p-toluenesulfonyl)-N-(2-fluoroethyl)aminomethyl]pyrrolidine (6.30 g).

A solution of this pyrrolidine in concentrated hydrochloric acid (100 ml) was refluxed for 23.5 hours and concentrated. To the residue was added concentrated hydrochloric acid (100 ml), refluxed for further 8 hours and concentrated. A solution of the residue in water washed with chloroform and the water layer was concentrated. The resulting residue was recrystallized from acetonitrile to give 1-benzyl-3-(2-fluoroethyl)aminomethylpyrrolidine hydrochloride (1.47 g), mp 212°–213° C.

Analysis (%) for $C_{14}H_{21}FN_2.2HCl.0.8H_2O$, Calcd. (Found): C, 51.95 (52.01); H, 7.66 (7.60); N, 8.66 (8.72).

To this salt (1.40 g) was added 25% aqueous solution of potassium carbonate (5 ml), extracted with chloroform, washed with 25% aqueous solution of potassium carbonate and water, dried over anhydrous sodium sulfate and concentrated to give 1-benzyl-3-(2-fluoroethyl)aminomethylpyrrolidine (1.05 g) as oil.

A suspension of this oil and 10% palladium-on-charcoal (0.51 g) in ethanol (25 ml) was shaken with hydrogen were absorbed under elevated pressure (100 kg/cm$^2$) for 9 hours. The catalyst was removed by filtration and the filtrate was evaporated to give 3-(2-fluoroethyl)aminomethylpyrrolidine (0.33 g) as red yellow oil.

EXAMPLE 1

8-Chloro-1-cyclopropyl-6-fluoro-7-[3-(2-fluoroethyl)aminomethyl-1-pyrrolidinyl]-1,4-dihydro-4-oxo-3-quinolinecarboxylic acid A suspension of 8-chloro-1-cyclopropyl-6,7-difluoro-1,4-dihydro-4-oxo-3-quinolinecarboxylic acid (200 mg), 3-(2-fluoroethylaminomethyl)pyrrolidine (165 mg) and 1,8-diazabicyclo[5,4,0]-7-undecene (DBU, 100 mg) in absolute acetonitrile (2 ml) was refluxed for an hour. After cooling, the reaction mixture was concentrated and to the residue was added acetonitrile-ether (1:1, 5 ml). The solution was allowed to stand overnight at 5° C., then the resulting precipitate was collected by filtration and recrystallized from chloroform-methanol-ether to give the title compound (40 mg), mp 138°–142° C.

Analysis (%) for $C_{20}H_{22}ClF_2N_3O_3.\frac{1}{2}H_2O$, Calcd. (Found): C, 55.24 (55.52); H, 5.33 (5.27); N, 9.66 (9.77).

EXAMPLE 2

1-Cyclopropyl-7-[3-(2-fluoroethyl)aminomethyl-1-pyrrolidinyl]-6,8-difluoro-1,4-dihydro-4-oxo-3-quinolinecarboxylic acid A suspension of 1-cyclopropyl-6,7,8-trifluoro-1,4-dihydro-4-oxo-3-quinolinecarboxylic acid (200 mg), 3-(2-fluoroethylaminomethyl)pyrrolidine (165 mg) and 1,8-diazabicyclo[5,4,0]-7-undecene (100 mg) in absolute acetonitrile (2 ml) was refluxed for an hour. After cooling, the reaction mixture was concentrated and to the residue was added acetonitrile-ether (1:1, 5 ml). The solution was allowed to stand overnight at 5° C., then the resulting precipitate was collected by filtration and recrystallized from chloroform-methanol-ether to give the title compound (140 mg), mp 134°–138° C.

Analysis (%) for $C_{20}H_{22}F_3N_3O_3.3/2H_2O$, Calcd. (Found): C, 55.04 (55.04); H, 5.77 (5.65); N, 9.63 (9.76).

Experiment 1

Antibacterial spectrum

Minimal inhibitory concentrations (MICs) were determined in accordance with the method recommended by Japan Society of Chemotherapy. The results are shown in Table 1.

TABLE 1

| Organism (10$^6$ cells/ml) | Gram | MIC (μg/ml) Exp. 1 | Exp. 2 | CPFX |
|---|---|---|---|---|
| In vitro antibacterial activity (aerobic bacteria) | | | | |
| Bacillus subtilis PCI 219 | + | ≦0.0063 | 0.0125 | 0.05 |
| Staphylococcus aureus 209 P | + | ≦0.0063 | 0.0125 | 0.20 |
| S. aureus Smith | + | ≦0.0063 | 0.0125 | 0.20 |
| S. aureus IID 670 (Terajima) | + | ≦0.0063 | 0.025 | 0.10 |
| S. epidermidis IID 866 | + | 0.0125 | 0.025 | 0.10 |
| Streptococcus pyogenes (S-8) | + | 0.025 | 0.05 | 0.39 |

TABLE 1-continued

| Organism (10⁶ cells/ml) | Gram | MIC (μg/ml) Exp. 1 | Exp. 2 | CPFX |
|---|---|---|---|---|
| S. pyogenes IID 692 | + | 0.05 | 0.10 | 0.78 |
| S. pneumoniae IID 552 | + | 0.025 | 0.05 | 0.78 |
| E. faecalis IID 682 | + | 0.05 | 0.10 | 0.78 |
| Escherichia coli NIHJ JC-2 | − | 0.0125 | 0.025 | ≦0.0063 |
| E. coli ATCC 10536 | − | 0.0125 | 0.025 | 0.025 |
| E. coli ML 4707 | − | 0.0125 | 0.025 | 0.0125 |
| Proteus vulgaris IFO 3167 | − | 0.025 | 0.05 | 0.025 |
| P. mirabilis IID 992 | − | 0.025 | 0.05 | 0.025 |
| Morganella morganii IID 602 | − | 0.10 | 0.20 | 0.05 |
| Klebsiella pneumoniae KY(GN)6445 | − | 0.05 | 0.05 | 0.025 |
| K. pneumoniae 1-220S | − | 0.10 | 0.10 | 0.05 |
| Enterobacter cloacae IID 977 | − | 0.10 | 0.10 | 0.05 |
| Citrobacter freundii IID 976 | − | 0.05 | 0.05 | 0.025 |
| Serratia marcescens IID 618 | − | 0.10 | 0.20 | 0.05 |
| S. marcescens GN 7577 | − | 1.56 | 1.56 | 0.39 |
| Shigella sonnei IID 969 | − | 0.0125 | 0.0125 | 0.0125 |
| Salmonella enteritidis IID 604 | − | 0.10 | 0.10 | 0.025 |
| Yersinia enterocolitica IID 981 | − | 0.10 | 0.10 | 0.05 |
| Pseudomonas aeruginosa V-1 | − | 0.39 | 0.39 | 0.05 |
| P. aeruginosa IFO 12689 | − | 1.56 | 1.56 | 0.39 |
| P. aeruginosa IID 1210 | − | 1.56 | 1.56 | 0.39 |
| P. cepacia GIFU 518 | − | 0.78 | 0.78 | 0.39 |
| P. maltophilia GIFU 2491 | − | 0.20 | 0.20 | 0.39 |
| Acinetobacter anitratus IID 876 | − | 0.05 | 0.05 | 0.20 |
| Alcaligenes faecalis 0114002 | − | 0.39 | 0.39 | 0.20 |
| In vitro antibacterial activity (anaerobic bacteria) | | | | |
| Bacteroides fragilis GM 7000 | − | ≦0.05 | 0.39 | 6.25 |
| B. fragilis 0558 | − | ≦0.05 | 0.39 | 3.13 |
| B. fragilis 25285 | − | ≦0.05 | 0.39 | 6.25 |
| B. distasonis 8503 | − | 0.20 | 0.78 | 6.25 |
| B. thetaiotaomicron (0661) | − | 0.20 | 0.78 | 12.5 |
| B. vulgatus KYA 29327 | − | ≦0.05 | 0.39 | 25 |
| B. melaninogenicus GAI 0410 | − | 0.10 | 0.39 | — |
| Fusobacterium mortiferum 4249 | − | ≦0.05 | 0.20 | 3.13 |
| F. necrophorum S-45 | − | 0.10 | 0.20 | 1.56 |
| F. varium KYA 8501 | − | 0.39 | 0.78 | 12.5 |
| F. nucleatum | − | ≦0.05 | 0.20 | — |
| Eubacterium limosum KYA 8486 | + | 0.39 | 0.78 | 3.13 |
| E. lentum GAI 5242 | + | 0.10 | 0.39 | 1.56 |
| Propionibacterium acens 11828 | + | 0.78 | 1.56 | 12.5 |
| Peptococcus magnus KY 017 | + | ≦0.05 | ≦0.05 | — |
| Clostridium difficile I-E | + | 0.20 | 0.78 | — |
| C. perfringens KYA 13123 | + | ≦0.05 | 0.10 | 0.39 |
| C. ramosum | + | 0.10 | 0.39 | 6.25 |
| Peptostreptococcus anaerobius KYA 27337 | + | ≦0.05 | ≦0.05 | 1.56 |
| Pst. micros UPI 5464-1 | + | 0.10 | 0.20 | 0.20 |
| Veillonella parvula KYA 10790 | − | 0.10 | 0.20 | 0.20 |
| In vitro antibacterial activity (clinical isolates) | | | | |
| S. pyogenes 3130 | | 0.025 | 0.05 | 0.39 |
| 3102 | | 0.025 | 0.05 | 0.39 |
| 3107 | | 0.025 | 0.05 | 0.39 |
| 4340 | | 0.025 | 0.05 | 0.39 |
| 4372 | | 0.025 | 0.05 | 0.78 |
| 3131 | | 0.025 | 0.05 | 0.39 |
| S. pneumoniae 15 | | 0.025 | 0.05 | 1.56 |
| 3727 | | 0.025 | 0.05 | 1.56 |
| 17 | | 0.025 | 0.05 | 1.56 |
| 2054 | | 0.025 | 0.05 | 1.56 |
| 4288 | | 0.025 | 0.05 | 1.56 |
| 2950 | | 0.025 | 0.05 | 0.78 |
| S. agalactiae 4394 | | 0.10 | 0.10 | 1.56 |
| 4049 | | 0.025 | 0.05 | 0.78 |
| 4342 | | 0.05 | 0.05 | 1.56 |
| 4470 | | 0.025 | 0.05 | 0.78 |
| 4368 | | 0.025 | 0.05 | 0.39 |
| 4468 | | 0.025 | 0.05 | 0.78 |
| E. faecalis 49 | | 0.05 | 0.05 | 1.56 |
| 214 | | 0.05 | 0.05 | 1.56 |
| 401 | | 0.05 | 0.10 | 1.56 |
| 402 | | 0.10 | 0.10 | 1.56 |
| 604 | | 0.05 | 0.10 | 0.78 |

CPFX: ciprofloxacin

What is claimed is:

1. A compound of the formula (I);

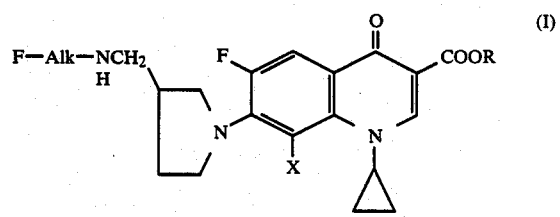

wherein R is hydrogen atom or lower alkyl group, Alk is lower alkylene group and X is hydrogen atom or halogen atom; the hydrates or the pharmaceutically acceptable acid addition or alkali salts thereof.

2. The compound of claim 1, wherein the compound is 8-chloro-1-cyclopropyl-6-fluoro-7[3-(2-fluoroethyl)aminomethyl-1-pyrrolidinyl]-1,4-dihydro-4-oxo-3-quinolinecarboxylic acid.

3. The compound of claim 1, wherein the compound is 1-cyclopropyl-7-[3-(2-fluoroethyl)aminomethyl-1-pyrrolidinyl]-6,8-difluoro-1,4-dihydro-4-oxo-3-quinolinecarboxylic acid.

4. An antibacterial pharmaceutical composition comprising an antibacterially effective amount of at least one compound according to claim 1 and an inert pharmaceutically acceptable carrier.

* * * * *